US00PP33617P2

(12) United States Plant Patent
O'Connell

(10) Patent No.: US PP33,617 P2
(45) Date of Patent: Nov. 2, 2021

(54) ***ECHEVERIA* PLANT NAMED 'ANGEL KISSED'**

(50) Latin Name: *Echeveria hybrida*
Varietal Denomination: Angel Kissed

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/130,663

(22) Filed: Dec. 22, 2020

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/12
See application file for complete search history.

*Primary Examiner* — Keith O. Robinson
(74) *Attorney, Agent, or Firm* — Cassandra Bright

(57) ABSTRACT

A new and distinct plant of *Echeveria hybrida* named 'Angel Kissed' is disclosed, characterized by a low growing morphology and an overall pink blush to the rosette. Plants are compact and grow robustly. Foliage grows in a very concentric formation and is colored greyed-green, overlaid with a pink blush and each leaf margined in pink and having a bright pink apical tip. *Echeveria* is a popular genus, typically produced as container plants for the patio or as landscape plants.

3 Drawing Sheets

Latin name of the genus and species: *Echeveria hybrida*.
Variety denomination: 'ANGEL KISSED'.

BACKGROUND OF THE INVENTION

The new cultivar, *Echeveria* 'Angel Kissed', is the product of a planned breeding program by the inventor. The new variety was selected as a seedling from an open pollination program. The open-pollination resulting in the new variety was made between 2012 and 2014 at a commercial nursery in Vista, Calif. The seed parent is the unpatented *Echeveria hybrida* cultivar known as 'Lola'. The pollen parent is unknown. The discovery was made during April of 2016, in Vista, Calif., at a commercial greenhouse.

Asexual reproduction of the new cultivar 'Angel Kissed' was first performed in Vista, Calif., at a commercial greenhouse, by vegetative offsets in May of 2016. *Echeveria* 'Angel Kissed' has since produced at least 11 generations and has shown that the unique features of this cultivar are stable and reproduced true to type.

SUMMARY OF THE INVENTION

The cultivar 'Angel Kissed' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ANGEL KISSED'. These characteristics in combination distinguish 'ANGEL KISSED' as a new and distinct *Echeveria* cultivar:

1. *Echeveria* 'Angel Kissed' is a compact *Echeveria* with a lower growing morphology, characterized by an overall pink blush.

2. *Echeveria* 'Angel Kissed' displays a very concentric formation of leaves that are greyed-green overlaid with a pink blush, each leaf margined in pink and terminating with a pink apical tip.
3. *Echeveria* 'Angel Kissed' is a strong and robust grower.
4. *Echeveria* 'Angel Kissed', due to its pink coloration, is an excellent choice as an accent to other *Echeverias* in blue and green hues when mixed in commercial trays, or used as an accent plant in the commercially popular succulent mixed plantings or succulent gardens, particularly in contrast with succulents with orange or yellow foliage.

PARENTAL COMPARISON

Plants of the new cultivar 'Angel Kissed' are similar to plants of the parent in most horticultural characteristics. However, plants of the new cultivar 'Angel Kissed' differ in the following:

1. *Echeveria* 'Angel Kissed' forms rosettes that are lower in morphology than those of *Echeveria* 'Lola'.
2. *Echeveria* 'Angel Kissed' exhibits a rosette color of greyed-green overlaid with a pink blush, whereas the rosette of *Echeveria* 'Lola' is a pale alabaster color, blushed with violet during times of stress.
3. *Echeveria* 'Angel Kissed' displays leaves margined in pink, terminating apically with pink, whereas *Echeveria* 'Lola' exhibits leaves with hyaline margins.
4. *Echeveria* 'Angel Kissed' is a robust grower, with fewer cultivation problems as found in *Echeveria* 'Lola'.

COMMERCIAL COMPARISON

The new cultivar 'Angel Kissed' can be compared to the commercial variety *Echeveria* 'Pink Diamond', U.S. application Ser. No. 17/130,625. Plants of the new cultivar 'Angel Kissed' differ in the following:

1. While both varieties are compact, *Echeveria* 'Angel Kissed' is lower growing than 'Pink Diamond'.
2. *Echeveria* 'Angel Kissed' does not have the hyaline margins found on 'Pink Diamond'.
3. *Echeveria* 'Angel Kissed' produces leaves that are less blunt at the apex.

The new cultivar 'Angel Kissed' can be compared to the unpatented *Echeveria* 'Perle von Nurnberg'. Plants of the new cultivar 'Angel Kissed' are similar to *Echeveria* 'Perle von Nurnberg' in most horticultural characteristics. However, plants of the new cultivar 'Angel Kissed' differ in the following:

1. *Echeveria* 'Angel Kissed' forms nearly stemless rosettes of a low morpholgy, whereas *Echeveria* 'Perle von Nurnberg' produces rosettes with more stem growth, eventually resulting in a more shrublike *Echeveria*.
2. *Echeveria* 'Angel Kissed' has a somewhat slower growth rate than does *Echeveria* 'Perle von Nurnberg'.
3. *Echeveria* 'Angel Kissed' exhibits bright pink margins and apical tip, whereas *Echeveria* 'Perle von Nurnberg' displays a nearly monotone colored rosette.
4. *Echeveria* 'Angel Kissed' exhibits resistance to the fungi *Rhizoctonia*, whereas *Echeveria* 'Perle von Nurnberg' can be subject to attack by the fungi *Rhizoctonia*, often leading to demise.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Echeveria* 'Angel Kissed'. Plants photographed are approximately 5 months from a rooted cutting.

DETAILED BOTANICAL DESCRIPTION

Figure 1:
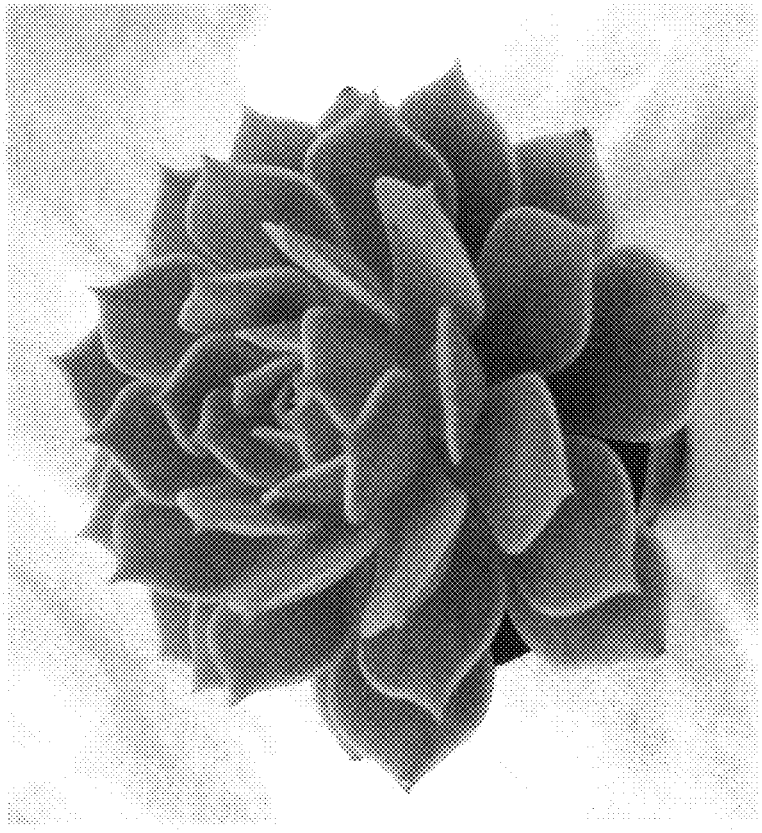
FIG. 1 illustrates in full color the rosette being described of *Echeveria* 'Angel Kissed', grown in a greenhouse (approximately 2100 foot candles) in Vista, Calif.
Figure 2:
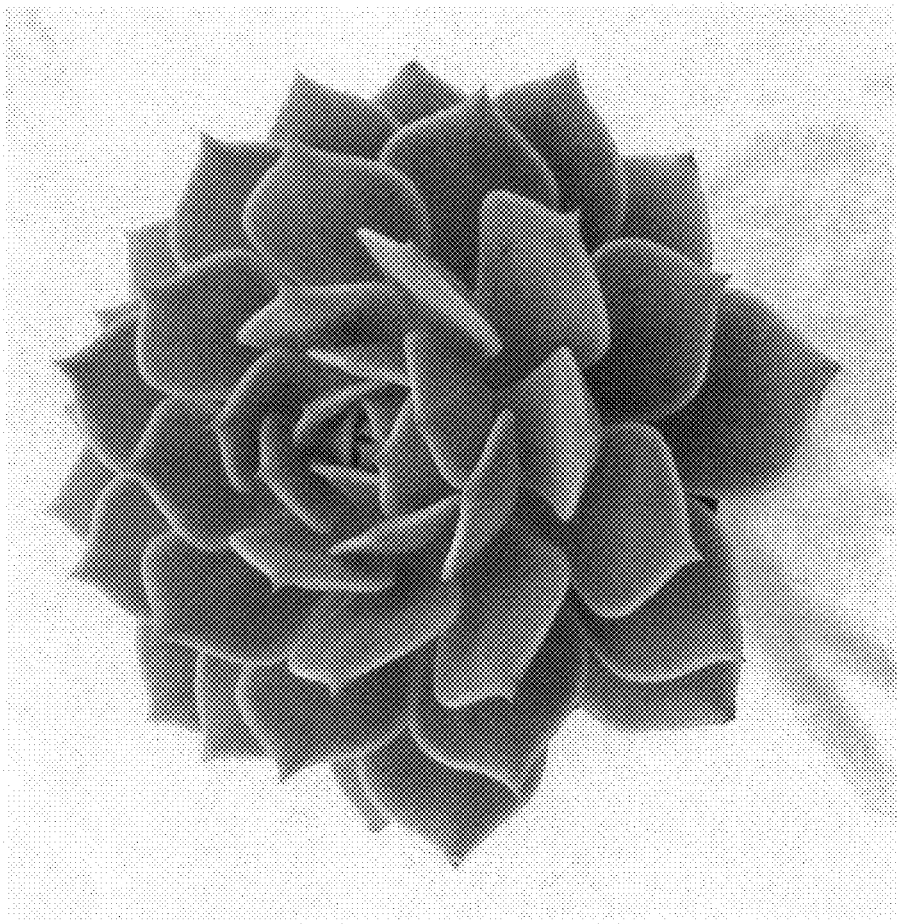
FIG. 2 illustrates in full color the rosette of a different angle of *Echeveria* 'Angel Kissed', grown in a greenhouse (approximately 2100 foot candles) in Vista, Calif.
Figure 3:
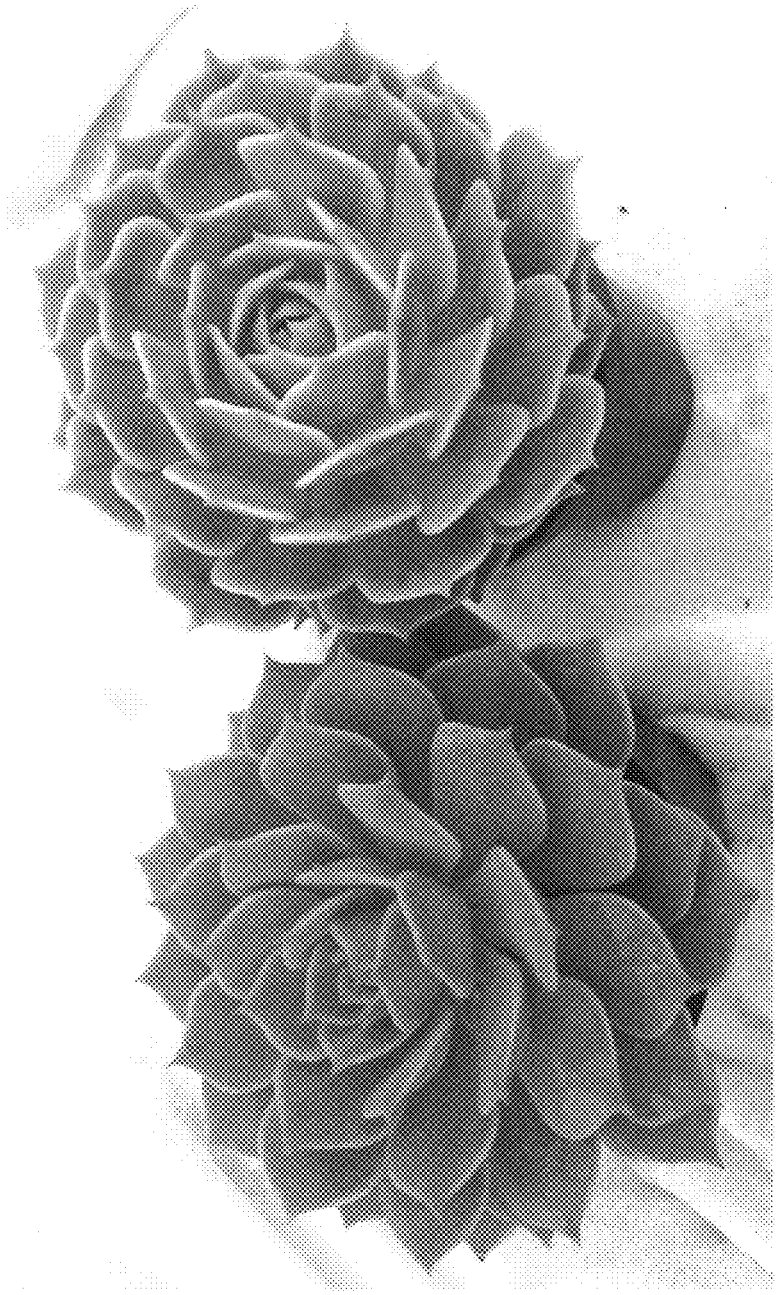
FIG. 3 illustrates in full color a comparison between *Echeveria* 'Lola;' and *Echeveria* 'Angel Kissed', grown in a greenhouse (approximately 2100 foot candles) in Vista, Calif.

In the following description, color references are made to The Royal Horticultural Society Colour Chart, 2007, except where general terms of ordinary dictionary significance are used. The following observations and measurements describe 'Angel Kissed' plants in a commercial greenhouse in Vista, Calif. Temperatures ranged from 2° C. to 38° C. night and day. No artificial light, photoperiodic treatments or chemical treatments were given to the plants. Natural light conditions were approximately 2500 fc of light. Measurements and numerical values represent averages of typical plant types.

Botanical classification: *Echeveria hybrida* 'ANGEL KISSED'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 12 cm.

Growth habit: Moderately dense, symmetrical rosette.

Height: Approximately 6 to 7 cm to top of highest leaf.

Plant spread: Approximately 13 cm.

Growth rate: Moderate to rapid.

Branching characteristics: Rosette forming, no branching.

FOLIAGE

Leaf:

*Arrangement*.—Rosulate.

*Quantity*.—About 70 to 85 per plant.

*Average length*.—Average range 3.5 to 5.7 cm.

*Average width*.—2.9 cm.

*Thickness*.—7 to 9 mm.

*Shape of blade*.—Spatulate.

*Apex*.—Apiculate. Slightly sharp.

*Base*.—Truncate.

*Margin*.—Entire.

*Aspect*.—Flat when mature, slightly concave younger foliage.

*Texture of top surface*.—Glabrous.

*Texture of bottom surface*.—Glabrous.

*Appearance of top surface*.—Matte, slightly glaucous.

*Appearance of bottom surface*.—Matte, slightly glaucous.

*Color*.—Young foliage upper side: Near Greyed-Purple N187D. Base near Green-White 157C. Margin Greyed-Purple 186A and 186B. Apical point colored near Red 53B. Young foliage, under side: Near Greyed-Purple N187D. Base near Green-White 157C. Margin Greyed-Purple 186A and 186B. Apical point colored near Red 53B. Mature foliage upper side: Near RHS Greyed-Green 191B. Base near Green-White 157C. Upper portion of blade flushed Greyed-Purple 184D. Margin and apex Red 50A. Mature foliage, under side: Near RHS Greyed-Green 191B. Base near Green-White 157C. Upper portion of blade flushed Greyed-Purple 184D. Margin and apex Red 50A.

*Venation*.—There is no visual appearance of venation.

FLOWER

None observed to date.

REPRODUCTIVE ORGANS

None observed to date.

OTHER CHARACTERISTICS

Fruits and seeds: Not observed.

Temperature tolerance: Tolerates temperatures from approximately −2° C. to at least 35° C.

Disease/pest resistance: Resistance observed to fungal diseases common with overwatering of *Echeveria* plants. Neither resistance or susceptibility to other normal diseases and pests of *Echeveria* has been observed. The pathogens of the fungal diseases cause leafspot in *Echeveria* are unconfirmed. Potential pathogens include *Alternaria* spp., *Bipolaris cactivori, Botrytis* spp., *Cladosporium tenuissimum, Colletotrichum* spp. and *Cercospora* spp.

Drought tolerance: Tolerates at least 3 weeks of high temperatures without supplemental water, showing no serious damage to plant.

What is claimed is:

1. A new and distinct cultivar of *Echeveria* plant named 'ANGEL KISSED' as herein illustrated and described.

* * * * *